(12) United States Patent
Dean et al.

(10) Patent No.: US 6,637,253 B2
(45) Date of Patent: Oct. 28, 2003

(54) HYDROGEN COLLECTION AND DETECTION

(75) Inventors: Frank William Houlton Dean, Cambridge (GB); Alan Edward Ling, Cambridge (GB)

(73) Assignee: Ion Science Limited, Cambridge (GB)

( * ) Notice: Subject to any disclaimer, the term of this patent is extended or adjusted under 35 U.S.C. 154(b) by 178 days.

(21) Appl. No.: 09/753,527

(22) Filed: Jan. 3, 2001

(65) Prior Publication Data

US 2001/0006008 A1 Jul. 5, 2001

(30) Foreign Application Priority Data

Jan. 5, 2000 (GB) ................................. 0000016

(51) Int. Cl.[7] .................... G01N 33/00; G01N 33/20; G01N 1/24
(52) U.S. Cl. .................. 73/23.2; 73/863.81; 73/864
(58) Field of Search .................. 73/23.2, 19.1, 73/31.01, 31.02, 31.03, 31.05, 31.07, 863.81, 863.83, 864, 864.73, 864.34

(56) References Cited

U.S. PATENT DOCUMENTS

| | | | | |
|---|---|---|---|---|
| 1,467,911 A | * | 9/1923 | Arendt et al. | 73/31.05 X |
| 2,400,940 A | * | 5/1946 | McCollum | 73/31.07 X |
| 2,660,053 A | | 11/1953 | Buehner | 73/40 |
| 2,751,281 A | * | 6/1956 | Cohn | 73/31.03 X |
| 2,921,210 A | * | 1/1960 | Schaschl et al. | 73/23.2 X |
| 3,242,717 A | * | 3/1966 | Matle et al. | 73/23.2 X |
| 3,927,555 A | * | 12/1975 | Godwin et al. | 73/23.2 X |
| 3,969,077 A | * | 7/1976 | Hill | 73/40.7 X |
| 4,181,005 A | * | 1/1980 | Kanegae et al. | 73/23.2 X |
| 4,820,920 A | | 4/1989 | Bather | 250/282 |
| 5,279,169 A | * | 1/1994 | Freeman | 73/86 X |
| 5,517,026 A | | 5/1996 | Sickenberger et al. | 250/288 |
| 5,551,310 A | * | 9/1996 | Formica et al. | 73/863.81 X |
| 6,216,526 B1 | * | 4/2001 | Junker et al. | 73/DIG. 9 X |
| 6,265,222 B1 | * | 7/2001 | DiMeo, Jr. et al. | 73/23.2 X |
| 6,277,329 B1 | * | 8/2001 | Evans | 73/19.1 X |

FOREIGN PATENT DOCUMENTS

| | | | | |
|---|---|---|---|---|
| EP | 6256 A1 | * | 1/1980 | G01N/1/00 |
| EP | 5 44 417 A1 | * | 6/1993 | G01N/1/00 |
| GB | 910359 | * | 11/1962 | |
| GB | 2312279 A | * | 10/1997 | G01N/33/20 |
| JP | 64-66537 | * | 3/1989 | 73/23.2 |
| JP | 2-140665 | * | 5/1990 | 73/19.07 |
| JP | 3-269234 | * | 11/1991 | 411/14 |

* cited by examiner

*Primary Examiner*—Thomas P. Noland
(74) *Attorney, Agent, or Firm*—Elman Technology Law, P.C.; Gerry J. Elman

(57) ABSTRACT

The present invention provides a hydrogen collector and detector system for detecting emanating hydrogen from the test surface of materials, a hydrogen collector for use in such a system and a method for using the hydrogen collector in such a system. The present collector comprises a flexible plate, which has constructed on its receptor face raised grooves or high spots. These are presented approximately parallel to an approximately flat test surface or approximately tangential to a curved test surface, and form guiding channels along which hydrogen emanating from the test surface can be drawn and sent to an associated detector system. For use on a magnetizable surface, the present collector plate may comprise magnets by which it can firmly yet removably be attached to the test surface.

26 Claims, 3 Drawing Sheets

ND DETECTION

CROSS REFERENCE TO RELATED APPLICATIONS

This application claims priority under 35 U.S.C. Section 119(a) from British Patent Application 00/00016.6, filed Jan. 5, 2000.

DETAILED DESCRIPTION

Overview

Figure 1:
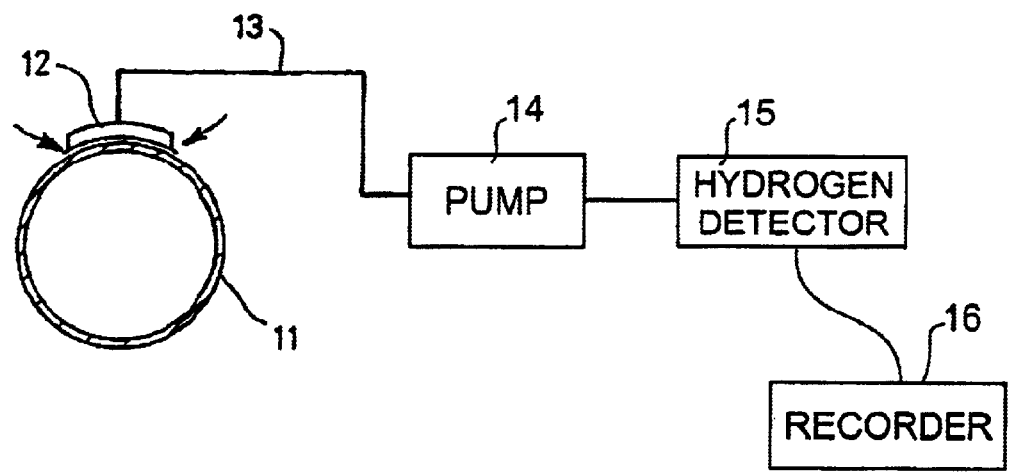
FIG. 1 shows a general view of the testing (for emanating hydrogen) of a surface in accordance with the invention.

This invention provides a system for the collection and detection of hydrogen in iron and steel and other materials. The invention also provides a method for the examination of iron and steel and other materials to determine whether these are giving off hydrogen gas, and therefore may be at risk from such problems as hydrogen embrittlement, Hydrogen is often inadvertently introduced to steel at high temperatures, such as in a melt, or during welding in a damp atmosphere. As the solubility of hydrogen in steel increases with temperature, supersaturation of hydrogen may occur when the metal cools. Supersaturation of hydrogen in steel may also occur upon corrosion, electroplating, and other surface treatments, or upon exposure of the steel surface to hydrogen sulphide, known chemically as $H_2S$, and often known otherwise as sour gas. Sour gas is often found in oil deposits, in the pipelines carrying oil and in petroleum products. Moreover, sour gas is often present in industrial-scale chemical reactions carried out in steel vessels and pipework or involving hydrogen and high temperatures and pressures, such as the hydrogenation of alkenes, a reaction which can result in deleterious hydrogen absorption by the steel.

In mild steels, that is untempered or not stainless steel, a large proportion of the hydrogen is free to diffuse throughout the steel, emanating at the steel surface. The measurement of this diffusible hydrogen in steel is very important, since the hydrogen embrittles the steel, lowering its tensile strength, and may ultimately cause the steel to blister or crack. These deleterious effects may be apparent only several days after the introduction of the hydrogen. Awareness that hydrogen persists in such a material is therefore of considerable value. The measurement of hydrogen flux, defined as flow of hydrogen per unit area, that emanates from a steel surface provides a qualitative indication of embrittlement and allows a means for quality control at various stages of steel processing and deployment. If the hydrogen flux is high, appropriate measures can be taken before the hydrogen leads to costly damage, such as a cracked steel pipeline or an embrittled weld.

Incorporated herein by reference is the specification of British Patent No: 2,312,279, which describes and claims a hydrogen detection system. This system is defined as one that detects the hydrogen emanating from the surface of a solid. The system comprises walls defining an open enclosure. During the process of hydrogen flux detection, the opening of the enclosure is closed by the test surface to be sensed for emanating hydrogen. The enclosure acts to gather the emanating hydrogen from the test surface into a carrier gas already present in the enclosure. The enclosure comprises input means for receiving the carrier gas and output means for delivering the resultant mixture of carrier gas and emanated hydrogen. A hydrogen detector connected to the enclosure output means and receives the mixture of carrier gas and emanated hydrogen.

In operation, the enclosure—hereinafter referred to as the "collector"—is pressed against the test surface from which hydrogen is thought to be emanating. Carrier gas is then drawn into the formed closed volume. Taking any hydrogen with it, the carrier gas is then passed on to the hydrogen detector apparatus. In one embodiment of the present invention, the carrier gas may be ambient air, to which is mixed any hydrogen emanating from the test surface.

The present invention provides a hydrogen collector-detector system, the hydrogen collector in such a system, and a method by which the collector can conveniently be attached to the test surface even when that surface is of a non-planar form so as to detect hydrogen emanating from the test surface.

The system of the present invention may be used in connection with flat surfaces, to which attachment of a collector can be carefully assured. However, there is a need for the convenient attachment and detachment of a collector to surfaces that are not flat, e.g., the curved surfaces of a pipe. It is desirable that a collector be properly attachable to surfaces having a curvature falling within quite a wide range. This will be better understood from the following discussion.

FIG. 1 shows a system of the present invention. Shown is a section of pipeline pipe 11 onto which a collector device 12 of the invention has been magnetically clamped. As illustrated by the arrows in FIG. 1, atmospheric air is drawn under and into the collector plate around its edges at the openings of the channels 17 (see FIG. 2C), and travels through end along to exit via the output means 13, carrying any emanated hydrogen with it. The air/hydrogen mixture is drawn on, by a pump 14, and then passed on to a hydrogen detector (15) and then discarded back to atmosphere. The detector's output is fed to a suitable measuring and recording device 16, and the collected data made ready for subsequent use.

Due to the manner in which it is introduced, hydrogen may emanate from, for example, a steel surface only in localized 'hotspots', and/or over infrequent and unpredictable periods of time. For example, in gas pipelines conveying oil volatiles, sour gas and water, hydrogen entry may be confined to puddles of water at the base of the pipe's interior. Eventually this hydrogen will exit at the pipe's exterior face, but exit not occur for several days. Indeed, the delay may vary over a timescale ranging from days to years as a consequence of the variable composition of the interior gas. In another example, during either routine or multipass welding, only an occasional weld may contain significant diffusible hydrogen due to a damp weld consumable. And in a further example, hydrogen may be introduced into cast steel from an occasional batch of molten steel that contained dissolved hydrogen sourced from one particular feedstock ingredient. It is therefore frequently necessary to carry out multiple tests on steel surfaces in search of prospective hydrogen flux over a period of time and over a range of surfaces. Such surfaces may be of variable surface geometry due to either unpredictable factors, as for example with steel plate milled to a flatness tolerance of no more than a few millimeters per meter, or to predictable factors, as is the case with steel pipes in a production plant whose diameters commonly vary by as much as from 10 to 100 cm.

Of course, to be both meaningful and useful, any hydrogen flux measurement must be reproducible. Intermittent testing for flux from a pipe surface over several months may provide an insight into progressive enhancement or attenuation of hydrogen entry at the pipe's interior only if the measurements are comparable. Over significantly long time periods, measurements become comparable when it is possible to assign, for a given steel and hydrogen entry regime, a critical flux at which hydrogen embrittlement may occur and a time when some remedial action should be undertaken.

The system of the present invention seeks to deal with the conformity problem by making a hydrogen collector flexible enough to fit the surface to which it is applied with little regard to the curvature of the surface. To render the collector conformable to surfaces of moderate curvature, the present invention provides a flexible collector. The receptor face of the collector has raised grooves or high spots, which may be presented approximately parallel to an approximately flat surface or approximately tangential to a curved surface. These grooves or high spots form guiding channels along which hydrogen emanating from the surface underlying the plate can be drawn and sent to the detector system. In some embodiments, the plate is elastically flexible.

Thus, the present invention provides a hydrogen collection and detection system, in which the collector comprises a flexible plate whose receptor face has constructed guide channels. Along these channels, hydrogen emanating from the test surface underlying the plate can be drawn and sent to the associated detector system. In providing a flexible collector plate that can be used to form an enclosure over a test surface when detecting hydrogen, which is the subject of the aforementioned Patent, the present invention has input means for receiving a carrier gas and output means for delivering the resultant mixture of carrier gas and emanated hydrogen, and which is operatively connected to a hydrogen detector for reception of the mixture of carrier gas and emanated hydrogen collected thereby and for the detection and measurement thereof.

Figure 2A:
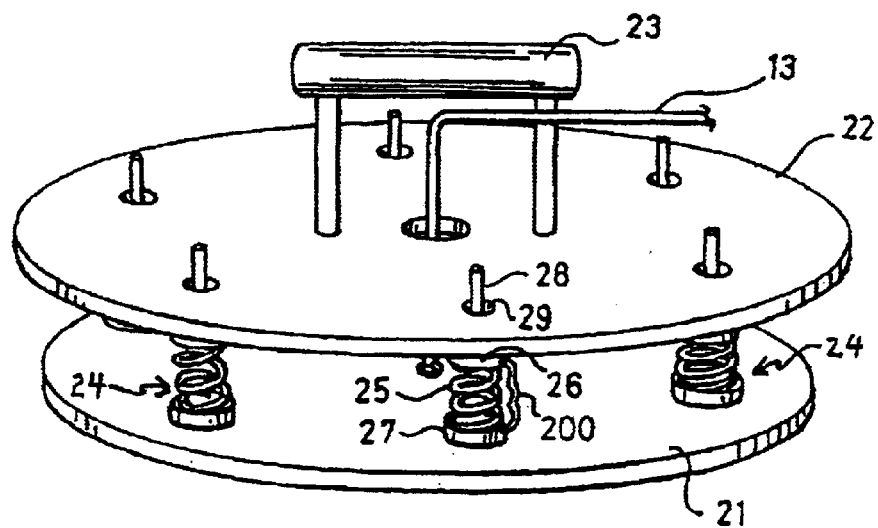
FIGS. 2A–C show views—perspective from above, side elevation, and top plan (in see-through)—of a collector device of the invention.
Figure 4:
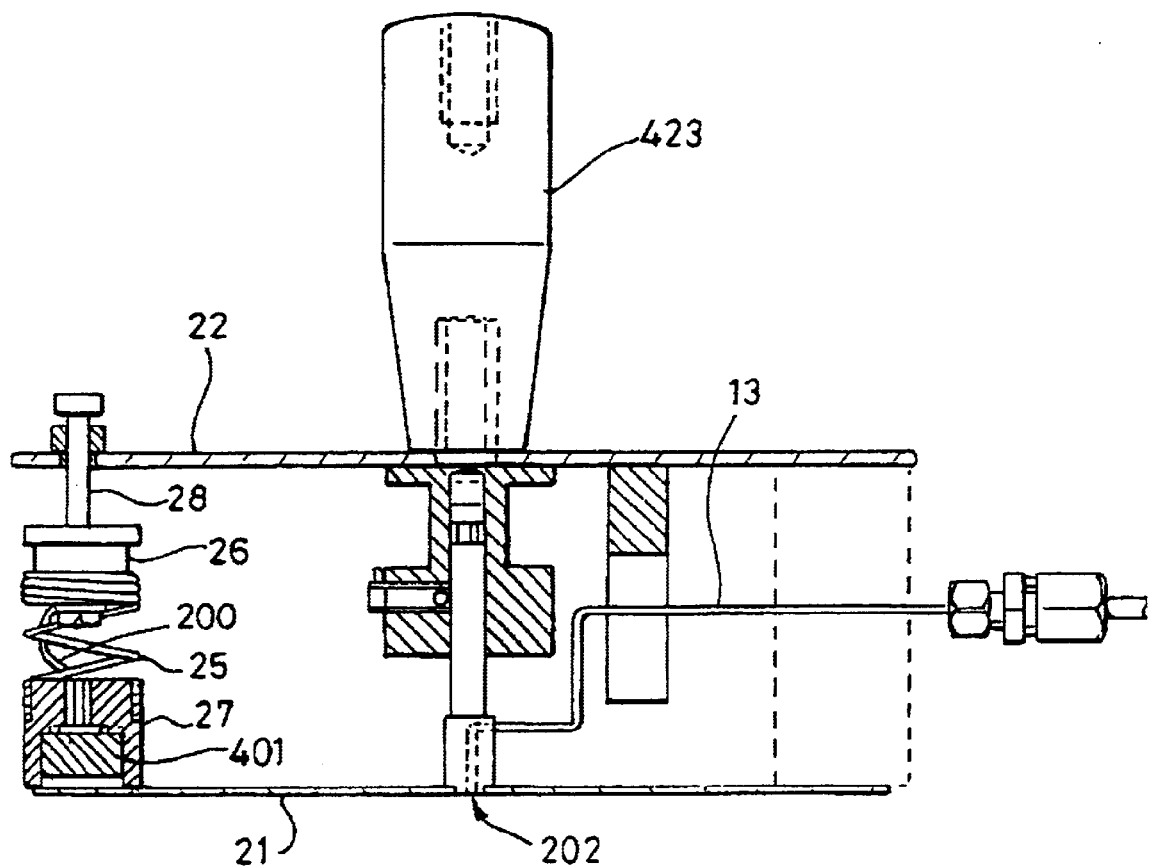
FIG. 4 shows, in side elevation (like FIG. 2B), part of a different embodiment of a device of the invention.

FIGS. 2A, B and C show one embodiment of the hydrogen collector of the present invention. FIGS. 2A & B show that a device of the present invention comprises a collector plate 21 mounted on a backplate 22 which bears a carrying handle 23. There are six individual mountings 24 for the collector plate 21; each mounting 24 comprises a spring 25 with a holder 26,27 at each end which is threaded so that the spring can be "wound" on to it. Holder 26 is supported on a rod 28 passing loosely through a bushed aperture 29 in the backplate 22; holder 27 carries recessed therein a magnet 401 (FIG. 4). The combination of rod 28 and spring 25 permits the bottom holder 27, and thus the magnet inside it, to move up and down and side to side, as required when the device is used and the collector plate 21 flexes into contact with a test surface. An inelastic tie, or string, 200 prevents the collector plate 21 being pulled too far from the backplate 22, and so stops the spring 25 from becoming over-extended.

Figure 2B:
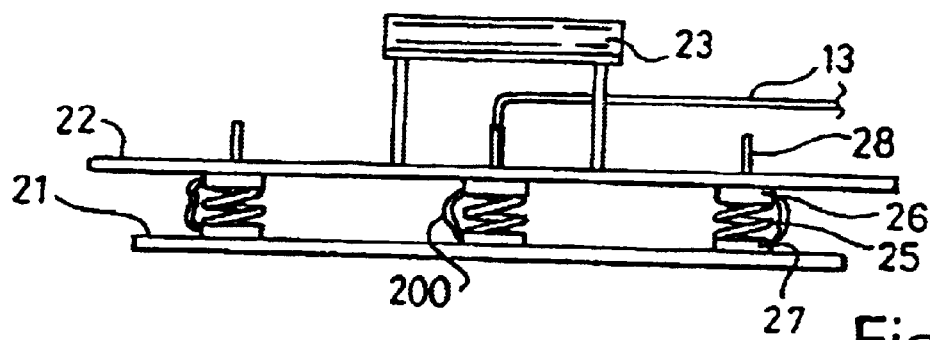
Figure 2C:
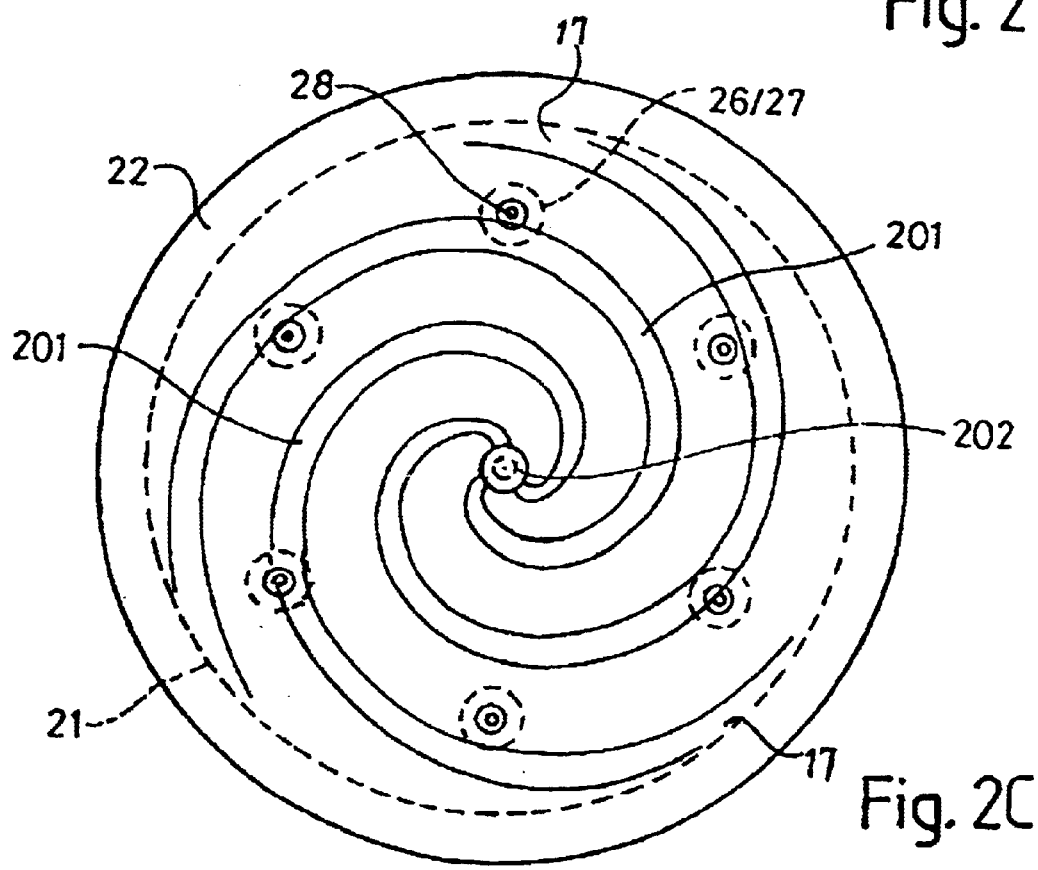

As shown diagrammatically in the top plan view of FIG. 2C, which shows an unhandled embodiment of the invention, the receptor face of the collector plate 21 is spirally grooved so as to define channels 201, bounded by low walls. The input means 17 for receiving a carrier gas are the openings in the plate channels through which the gas enters the channels. It is along channels 201 that air and emanated hydrogen are drawn in to a centrally located point, and then, through an opening 202, connected to the output means 13. From there the emanated hydrogen and air are drawn out of the collector plate 21 and on to the detector 15 (FIG. 1.)

The plate material of the collector of the present invention is any that is sufficiently flexible. A particular embodiment of the present collector is elastically flexible, so that it will recover its own, basic shape without the need for any intervention. The elastically flexible material will allow the plate to bend to the shape of the surface against which it is used but which will not allow the collected hydrogen to diffuse through and so be lost before detection and measurement. Embodiments of the plate body are made of a metal, a metallized plastic, or a plastic/metal laminate. The dimensions—and specifically the thickness—of the plates are such as to afford it the desired flexibility. One embodiment of the plate of the present invention is stainless steel, being particularly tough and sufficiently flexible to be suitable. Other embodiments of the plate of the present invention are made of plastic.

The gas is gathered into, and swept along, channels formed in the receptor face of the plate. High spots in the receptor face effectively form walls that define the channels. Efficient sweeping of gas from the space confined between the test surface, the plate face and the high spots necessitates limited plate contact with the test surface, so that the grooves walls/high spots are inevitably under considerable compression when the plate is up against the test surface. When the plate is pressed against the test surface, the openings of the channels 17 form the input means by which the carrier gas is channelled around the plate towards the centrally located egress.

Plastics and plastic laminates are more likely to be damaged by rough contact with the test surface than metal, especially when the collector is inadvertently dragged across the surface by the operator. Therefore, in certain applications, a tough, flexible and elastically-deformable groove wall made of a deformable plastic may ensure a good seal between the plate/steel contact surface, and therefore increase the reproducibility of measurement.

In the stainless steel embodiments, the plate is comprised entirely of sheet stainless steel into which the collecting grooves are formed. The steel may be untempered, so as to retain its flexibility characteristics. A convenient way to form the required grooves is by chemical etching, by leaving the wall portions behind. Chemical etching provides a practical and inexpensive plate with sufficient toughness to endure numerous hydrogen flux tests even on rough surfaces, as commonly encountered when testing, for instance, a steel pipeline pipe for the conveyance of gas sourced from sour oil.

The collector plate of the present invention may be of any size appropriate to its intended purpose. For attachment to a surface of a curvature corresponding to that of a cylindrical surface, like a pipeline pipe, of from 30 cm (about 1 ft) diameter and above, a plate of 15 cm (about 6 in) diameter is generally satisfactory. Such a plate conveniently contains collector channels defined by walls of 0.5 mm (0.02 in) width and 0.2 mm (0.01 in) height. The plate body is preferably about 0.2 mm (0.01 in) thick. A plate that is significantly thicker is rather difficult to flex into contact with the test surface, while a significantly thinner plate is not likely to be sufficiently robust to withstand the rough conditions commonly prevailing in the collector's deployment.

The guide channel structure geometry may be any suitable. The point in the plate 202 to which the collected hydrogen is delivered for onwards passage is located about the center in the plate. Thus the channels 201 are most conveniently either radial or a single spiral terminating about at the center of the plate. The gap between adjacent grooves is about 1 cm (0.4 in).

The actual output means 13 (FIGS. 2A & 2B) by which the gas exits the plate may be a capillary piping leading off to a remote detector and pump. For a 15 cm (6 in) diameter plate, the union between the gas exit means and the collector plate is minimal so as not to limit significantly the collector plate's flexibility.

In use, the plate 21 is held against the test surface firmly and securely for some period of time sufficient to collect enough hydrogen for the purpose of the test. To assist in this, then, the collector plate 21 may be first supported on a backing plate 22, which is attached on that surface of the collector plate opposite the receptor face, as shown in FIG. 2A. The support provided by the backing plate will permit the required flexing of the collector plate to occur when the combination 21 and 22 is pushed into operative contact with a curved test surface. For example, the backing plate is conveniently a relatively rigid member to which the collector plate is attached by any of a flexible, bendable, pivotable, floating mounting means 24 disposed around the peripheries of both plates, leaving the center of the collector plate free. The mounting means 24 could be rubber pads, springs, or some combination of these.

As shown in FIG. 2A, one embodiment of a mounting means is a combination of a support rod 28 loosely mounted, in an oversize bush 29, in the backing plate 22, the rod 28 carrying at its free end one end of a spring 25 to the other end of which the collector plate is mounted. A plurality of these mounting means 24, spaced uniformly around the peripheries of the two plate combination, causes the collector plate 21 to be supported on the backing plate 22 so that it can flex sufficiently freely when offered up to a curved test surface.

As noted above, during testing, the collector plate must be held up against the test surface firmly and securely for some time. To facilitate utilization of the present invention, the backing plate can be provided with a handle (FIGS. 2A & B), or some other means by which it can be grasped. A long handle may be useful to assist in locating the collector plate against a distant, hard-to-reach surface, or against some surface that is, for example, too hot to allow the operator to get close.

Moreover, since the collector plate may need to be held in position for an hour or so, it may be more advantageous to the operator not to hold the collector by hand but to clamp it in position. One embodiment attains the required end of clamping by magnetic action. Most commonly the surfaces—for example, the steel surfaces—from which hydrogen emanates are magnetic. Non-magnetic steels are austenitic and effectively hydrogen impermeable. A magnetic means of attachment of the collector plate therefore may be viable in many of the instances where detection or measurement of emanating hydrogen is of interest. Magnetic clamping may be achieved by placing a plurality of magnets 401 (FIG. 4) on the surface of the collector plate opposite the receptor face and spaced around the peripheral area (See FIGS. 2A, 2B & 3). By using reasonably strong magnets, the magnetic field of each is easily capable of extending during testing through the plate and to the underlying test surface, thereby clamping the plate onto the surface indefinitely.

Figure 3:
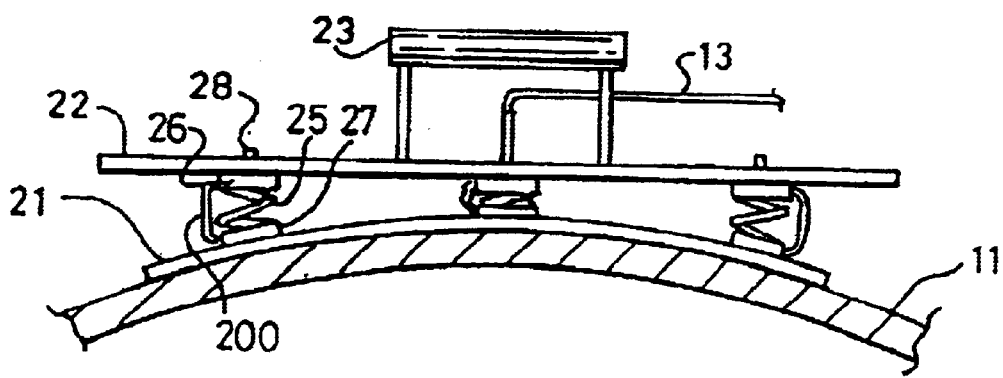
FIG. 3 shows in side elevation the device of FIG. 2B in use on a pipeline pipe.

FIG. 3 shows the collector device of the invention in use on a pipeline pipe 11. FIG. 3 illustrates how the clamping magnets 401 (FIG. 4) cause the collector plate 21 to flex into contact with the pipe 11, the rod and spring combination 28/25 allowing the magnets, in their holders 27, to move up and down and from side to side, so as the better to conform. The magnets 401 are advantageously retained on the collector plate 21 by being mounted on the backing plate 22 as to afford them limited vertical and rocking movement. As noted above, one embodiment of a mounting means 24 for the collector plate 21 on the backing plate is a combination of a support rod 28 loosely mounted in the backing plate 22 and carrying at its free end a spring 25 on which the collector plate is mounted. If the spring 25 bears the magnet 401 at its free end, then the resultant plurality of these combinations 24, spaced uniformly around the two plates' peripheries, causes the collector plate 21 to be supported on the backing plate 22 so that it can flex freely as desired when offered up to a curved test surface and yet be clamped to that surface by the magnets. If the magnets are sufficiently strongly attracted to the test surface, then they will bend the collector plate towards that surface. As the plate 21 bends, and the distance between each magnet and the test surface decreases, so the attraction between each magnet 401 and the surface increases, facilitating further deformation of the plate 21 until the plate 21 is firmly attached to the steel. The spring/bush mounting 25,28 enables the magnets 401 to twist as necessary to ensure their approximately closest approach to the plate.

FIG. 4 shows an alternative embodiment of the collector device of the present invention. This embodiment has a different carrying handle 423. Shown also is the magnet 401 recessed within the bottom holder 27, the rod 28 in its hole in the backplate 22, the spring 25 "wound" around the threaded top and bottom holders 26,27, and the string tie 200 between those two holders.

In practice most metal surfaces to be tested will be covered in a paint layer one or two millimeters thick. To provide some uniformity in the magnetic forces involved, it is therefore preferred to utilize very strong magnets positioned such that they cannot actually come into "direct" contact with the surface. For a strong magnet at some distance from the surface, the useful attractive forces change less rapidly with distance than for a weak magnet at some shorter distance at which these forces are achieved. Each magnet may itself be individually mounted in a small holder such that its active end is recessed, and may never actually come into contact with the collector plate back. The holder itself will contact the plate's back, and may preferably be of a "slippery" material, such as polytetrafluoroethylene [PTFE], to assist it to move laterally across the plate's back surface as will be required as the plate flexes. In this way, very powerful magnets can be used, to ensure sufficient flexing of the plate round high curvature surfaces, but the plate, and its magnets, can always relatively easily be freed from the steel after the test is complete.

In some embodiments there may be only two magnets at the perimeter and extreme ends of a collector plate to provide plate deformation to a steel surface. However, in the case of attachment to steel of cylindrical symmetry, such as a pipe, the embodiment of two magnets will only enable complete plate to surface contact if the collector is oriented so that magnets are in the plane of the cylinder cross-section. To enable fully acceptable test surface attachment irrespective of orientation, an embodiment with a minimum of six magnets is preferable, the magnets being arranged in a ring about the periphery of the collector plate, equidistant from each other and thus, generally at the points of a hexagon. The magnets may be disc shaped, having both their axis of cylindrical symmetry and North-South poles directed normal to the plate surface. The North-South poles of all the magnets may be parallel. This ensures mutual repulsion between the magnets, which assists their symmetrical and uniform deformation and reduces the effect of the poles between any two neighboring magnets being reversed, which would result in the magnets deforming unpredictably and with a tendency to 'pair up'.

One example of a flat collector plate of about 15 cm (6 in) diameter made to conform to an approximately 30 cm (12 in) diameter pipe requires maximum plate displacement of about 6 mm (0.25 in) at the perimeter. An exemplary 0.5 mm (0.02 in) thickness of the plate including the groove walls, and an exemplary 2.5 mm (0.1 in) thickness of paint on the pipework may call for a magnet facilitating plate movement at a maximum distance of some 9 mm (0.35 in). This is readily achieved with high power magnets of small dimensions, such as 7 mm (0.27 in) thickness, 14 mm (0.55 in) diameter, nickel-coated neodymium boron magnets whose poles are co-axial with the center of symmetry as described above.

As noted above, each magnet 401 is conveniently secured in a holder 26, 27 which may be a cradle or cup. The magnet may be positioned there by glue, by using a circlip, or by being a push fit. The magnet is recessed slightly in the holder so that attachment of the plate to an uncoated steel surface is not so strong as to make detachment difficult. In the case of the disc magnets mentioned above, a recess of 1 mm (0.04 in) in the holder is sufficient to enable excellent attachment of the plate described above to 30 cm (12 in) diameter steel pipework. The holder lip which contacts the plate is preferably rounded (and as noted before made of a material which readily slips against the plate), so that any angular movement of the holder necessary in securing the plate to a curved test surface is facilitated. The holder material may be non-magnetic, tough and readily machined. PTFE is a suitable material for this purpose.

The invention provides for magnetic movement to ensure plate conformation to any reasonable test surface no matter what its curvature. The means of this movement may, as indicated hereinbefore, be any suitable, and may comprise any of a combination of flexible arms, ball and socket joints, springs, levers or slots. When using a magnet holder such as the holder discussed above, the holder's exterior may be conveniently machined with a screw thread so to accommodate a spring, which may permit a rocking movement simply by the spring being "wound" onto the holder. At the other end of the spring, an end piece similarly machined to accommodate the spring may be attached to an arm which moves through a bushed slot in the backplate, enabling free vertical movement. A non-extensible string 200 (FIG. 2B) between the two holder parts prevents over-stretching of the spring during detachment from a steel surface.

Finally, the collector plate may be provided with a skirt at or just beyond its perimeter to prevent during use the ingress of water between the plate and steel, or provide limited protection of the plate edge.

In use, the collector plate of the invention collects the hydrogen gas that emanates from the test surface. The following equation measures the flux of hydrogen from the surface as (J) the flow per unit area, and shows J to be related to the measured concentration (C) of hydrogen entrained in the carrier gas (C), the carrier gas flow (F), and the effective area ($A_{eff}$):

$$J=(F \times C)/A_{eff} \quad \text{(i)}$$

What follows is a discussion of the optimal physical conditions to enable meaningful measurement. A significant flux of emanating hydrogen, J, is commonly very small. For example, in sour gas corrosion of pipework, the walls of the pipe often about order 1 cm (0.4 in) thick, and a significant flux is deemed to be of the order of a few thousand millionths of a cubic centimeter of hydrogen per square centimeter of surface per second ($pl/cm^2/s$). Thus, from Equation (i) it is preferable to measure the hydrogen concentration C captured in the gas steam to as low a threshold as possible. This sensitivity limit is constrained—by the concentration of hydrogen in air (0.5 ppm at sea level), and by the limits of the present technology—to about 0.1 ppm hydrogen.

Next, it is preferable to minimize the carrier gas flow F. Essentially, the lower the flow of carrier gas across the test surface the greater is the hydrogen enrichment as a given hydrogen flux is entrained into it. However, if that gas flow is too low, the hydrogen in the carrier gas stream is liable to back diffuse, that is, to move against the prevailing gas stream, thus lowering $A_{eff}$ for a particular collecting device. A very low flow will also significantly delay the hydrogen in its journey to the detector, particularly if the distance between the collector and detector exceeds one meter, as may be desirable in testing steel surfaces whose proximal air temperatures exceed what can be tolerated by a particular detector. A typical adequate flow for a collector of 15 cm (6 in) diameter is about 0.5 $cm^3/s$.

Finally, it is preferable to maximize $A_{eff}$. At a flow rate of 0.5 $cm^3/s$, about 70% of the hydrogen emanating from a smooth flat steel surface zone circumscribed by a circle of diameter 15 cm (6 in) is captured by a collector of similar dimensions, thus $A_{eff}$ in this case is about 100 $cm^2$. Drawing ambient air into a detector capable of resolving 0.2 ppm hydrogen, the minimum resolvable flux according to equation (i) is therefore:

$$0.5 \times 0.2 \times 10^{-6}/100 \; pl/cm^2/s = 1 \; pl/cm^2/s.$$

In the above embodiment, the collector may be of dimensions convenient for manual manipulation, but in many instances the test surface geometry will constrain the collector's maximum size. Conversely, in one application, namely that relating to the testing of high-pressure hydrogen entry into reformer vessels in petrochemical production, due to the high pressures involved the steel walls may be very thick, often 5 cm (2 in) as compared with 1 cm (0.4 in) for pipelines. In such cases, hydrogen emanation lower than 1 $pl/cm^2/s$ may be significant and require a larger collector (say, of diameter 30 cm (12 in).

What is claimed is:

1. A hydrogen collection and detection system comprising:
    a hydrogen collector; and
    a hydrogen detector,
    said hydrogen collector comprising a flexible collector plate, input means for receiving a carrier gas, and output means for delivering a mixture of the carrier gas and emanated hydrogen and being operatively connectable from the output means to said detector;
    said flexible collector plate being deformable to conform to a curved test surface;
    said flexible collector plate having a receptor face with guide channels along which said mixture of carrier gas and emanated hydrogen may be channelled and sent to said detector; said hydrogen detector being connected to the output means of the flexible collector plate so as to receive the mixture of the carrier gas and emanated hydrogen delivered from the output means of the flexible collector plate; and further comprising a backing plate and supports for supporting the flexible collector plate on the backing plate, said supports permitting flexing of the flexible collector plate when the combination of flexible collector plate and backing plate is pressed into operative contact with a curved test surface.

2. The system of claim 1, wherein the backing plate is a relatively rigid member to which the flexible collector plate is attached by a mounting means disposed around the periphery of the backing plate and around the periphery of the flexible collector plate.

3. The system of claim 2, wherein each mounting means comprises a support rod having a free end and another end and an oversize bush in the backing plate, the rod being mounted in the bush, and the rod carrying at its free end a spring and the flexible collector plate being mounted onto its other end.

4. The system of claim 2, wherein the flexible collector plate further comprises associated clamping means to hold the flexible collector plate against the test surface during hydrogen collection and detection.

5. The system of claim 4, wherein the clamping means comprise a plurality of magnets on the surface of the flexible collector plate opposite to the receptor face.

6. The system of claim 5, wherein each magnet is mounted on the backing plate by magnet mounting means that afford limited vertical and rocking movement.

7. The system of claim 6, wherein each magnet is individually mounted in a holder such that the active end of the magnet is recessed in the holder, whereby the active end of the magnet is prevented from coming into contact with the flexible collector plate.

8. The system of claim 1 wherein the guide channels comprise a geometry that forms a single spiral terminating near the center of the flexible collector plate.

9. The system of claim 8, wherein the backing plate is a relatively rigid member to which the flexible collector plate is attached by a mounting means disposed around the periphery of the backing plate and around the periphery of the flexible collector plate.

10. The system of claim 9, wherein each mounting means comprises a support rod having a free end and another end and an oversize bush in the backing plate, the rod being mounted in the bush, and the rod carrying at its free end a spring and the flexible collector plate being mounted onto its other end.

11. The system of claim 1 wherein said flexible collector plate is elastic.

12. A hydrogen collection and detection system comprising:
   a hydrogen collector; and
   a hydrogen detector,
   said hydrogen collector comprising a flexible collector plate, input means for receiving a carrier gas, and output means for delivering a mixture of the carrier gas and emanated hydrogen and being operatively connectable from the output means to said detector;
   said flexible collector plate being deformable to conform to a curved test surface;
   said flexible collector plate having a receptor face with guide channels along which said mixture of carrier gas and emanated hydrogen may be channelled and sent to said detector; said hydrogen detector being connected to the output means of the flexible collector plate so as to receive the mixture of the carrier gas and emanated hydrogen delivered from the output means of the flexible collector plate
   wherein the flexible, collector plate further comprises associated clamping means to hold the flexible collector plane against the rest surface during hydrogen collection and detection.

13. The system of claim 12, wherein the clamping means comprise a plurality of magnets on the surface of the flexible collector plate opposite to the receptor face.

14. The system of claim 13, wherein each magnet is mounted on the backing plate by magnet mounting means that afford limited vertical and rocking movement.

15. The system of claim 14, wherein each mounting means comprises a support rod having a free end and another end and an oversize bush in the backing plate, the rod being mounted in the bush, and the rod carrying at its free end a spring and the flexible collector plate being mounted onto its other end.

16. The system of claim 15, wherein each magnet is individually mounted in a holder such that the active end of the magnet is recessed in the holder, whereby the active end of the magnet is prevented from coming into contact with the flexible collector plate.

17. The system of claim 16, wherein there are at least six magnets arranged in a ring about the periphery of the flexible collector plate.

18. The system of claim 17, wherein each magnet is disc shaped and positioned with its axis of cylindrical symmetry and its North-South poles directed perpendicularly to the surface of the flexible collector plate, and with the North-South poles of all magnets being parallel.

19. The system of claim 12, wherein the guide channels comprise a geometry that forms a single spiral terminating near the center of the flexible collector plate.

20. The system of claim 19, wherein the clamping means comprise a plurality of magnets on the surface of the flexible collector plate opposite to the receptor face.

21. The system of claim 20, wherein each magnet is mounted on the backing plate by magnet mounting means that afford limited vertical and rocking movement.

22. The system of claim 21, wherein each mounting means comprises a support rod having a free end and another end and an oversize bush in the backing plate, the rod being mounted in the bush, and the rod carrying at its free end a spring and the flexible collector plate being mounted onto its other end, and wherein the spring bears the magnet at its free end.

23. The system of claim 22, wherein there are at least six magnets arranged in a ring about the periphery of the flexible collector plate.

24. A method of detecting hydrogen emanating from a surface, utilizing a hydrogen collection and detection system comprising: a hydrogen collector; and a hydrogen detector, said hydrogen collector comprising a flexible collector plate, input means for receiving a carrier gas, and output means for delivering a mixture of the carrier gas and emanated hydrogen and being operatively connectable from the output means to said detector; said flexible collector plate being deformable to conform to a curved test surface; said flexible collector plate having a receptor face with guide channels along which said mixture of carrier gas and emanated hydrogen may be channelled and sent to said detector; said hydrogen detector being connected to the output means of the flexible collector plate so as to receive the mixture of the carrier gas and emanated hydrogen delivered from the output means of the flexible collector plate, comprising the steps of
   a) operatively applying the hydrogen collection and detection system to a curved test surface, b) allowing a carrier gas to mix with hydrogen emanating from the surface, c) channeling the mixture of carrier gas and emanated hydrogen between the receptor face of the flexible collector plate and the test surface towards the output means, d) carrying the mixture via the output means to a collection vessel, and e) performing an analysis of the mixture to determine the hydrogen flux, wherein the hydrogen collection and detection system further comprises a backing plate and a plurality of supports the supporting the flexible collector plate on the backing plate, mounting means for attaching the flexible collector plate to the backing plate, clamping means associated with the flexible collector plate to hold the flexible collector plate against the test surface, wherein the clamping means comprise a plurality of magnets on the surface of the flexible collector plate opposite to the receptor face.

25. The method of claim 24, wherein the mounting means comprises a combination of a support rod mounted in the backing plate and carrying at a free end thereof a spring on which the flexible collector plate is mounted, wherein the spring bears one of said plurality of magnets on a free end thereof and whereby each magnet is individually mounted in a holder.

26. The method of claim 24, wherein the guide channels of the receptor face comprise a geometry that forms a single spiral terminating near the center of the flexible collector plate.

* * * * *